(12) United States Patent
Kadobayashi et al.

(10) Patent No.: US 8,494,241 B2
(45) Date of Patent: Jul. 23, 2013

(54) OCCLUSION EVALUATION APPARATUS AND OCCLUSION EVALUATION METHOD (75) Inventors: Yusei Kadobayashi, Kyoto (JP); Masako Shigezawa, Kyoto (JP); Keiji Takahashi, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 0 days.

(21) Appl. No.: 13/569,581

(22) Filed: Aug. 8, 2012

(65) Prior Publication Data

US 2013/0045458 A1 Feb. 21, 2013

(30) Foreign Application Priority Data

Aug. 18, 2011 (JP) ................... 2011-178906

(51) Int. Cl.
*G06K 9/00* (2006.01)
(52) U.S. Cl.
USPC ............. 382/128; 382/132; 382/154; 433/29; 433/30; 433/197; 433/68; 433/215
(58) Field of Classification Search
USPC ............. 382/128, 132, 254; 433/29, 30, 197, 433/68, 215
See application file for complete search history.

(56) References Cited

U.S. PATENT DOCUMENTS

| | | | |
|---|---|---|---|
| 7,283,654 B2 * | 10/2007 | McLain | 382/128 |
| 2011/0045441 A1 * | 2/2011 | Kadobayashi | 433/197 |
| 2011/0287381 A1 * | 11/2011 | Sanders | 433/75 |

FOREIGN PATENT DOCUMENTS

| | | |
|---|---|---|
| JP | 2005-193028 | 7/2005 |
| JP | 2005-237710 | 9/2005 |
| JP | 2008-220600 | 9/2008 |

OTHER PUBLICATIONS

Japanese Office Action issued Oct. 4, 2011 in Japanese Patent Application No. 2011-178906 along with English translation.
Japanese Office Action issued Jan. 10, 2012 in Japanese Patent Application No. 2011-178906 along with English translation.
Guideline for masticatory disturbance evaluation method—primarily method for measuring a masticatory ability-, Prosthodontic Journal, 2002, vol. 46, No. 4, pp. 619-625 along with partial English translation.

* cited by examiner

*Primary Examiner* — Ali Bayat
(74) *Attorney, Agent, or Firm* — Wenderoth, Lind & Ponack, L.L.P.

(57) ABSTRACT

An occlusion evaluation apparatus capable of evaluating a masticatory ability depending on an occlusal geometry of teeth without actually used by a human subject, reads three dimensional data of geometries of maxillary molar teeth 1, 2, 3, 4 and mandibular molar teeth 5, 6, 7, 8, and specifies a geometry of a fluxion space Va defined by a plane Sa which includes two adjacent contact points Pa between the maxillary molar teeth 1, 2, 3, 4 and mandibular molar teeth 5, 6, 7, 8 and which is perpendicular to the occlusal plane, the occlusal surfaces of the maxillary molar teeth 1, 2, 3, 4, and the occlusal surfaces of the mandibular molar teeth 5, 6, 7, 8.

13 Claims, 5 Drawing Sheets

OCCLUSION EVALUATION APPARATUS AND OCCLUSION EVALUATION METHOD

TECHNICAL FIELD

The present invention relates to an occlusion evaluation apparatus and an occlusion evaluation method.

BACKGROUND ART

As a method for measuring a masticatory ability of teeth (natural teeth and artificial teeth), as described in JP-2005-237710-A, JP-2008-220600-A and "Guideline for masticatory disturbance evaluation method-primarily method for measuring a masticatory ability—", Prosthodontic Journal, 2002, vol. 46 no. 4, p. 619-625, it is introduced a method for determining a masticatory ability by means that a human actually masticate something.

With such method, an effect of a muscular power, a chewing habit and the like of a human subject, and an effect of an occlusal geometry of teeth (including artificial teeth) can not be separately measured. Especially, at fabrication or adjustment of an artificial tooth, it is preferable that a masticatory ability resulted from an occlusal geometry of the artificial tooth can be independently evaluated.

In natural teeth, a maxillomandibular occlusal condition according to a crowding condition of teeth and a wear of teeth with aging significantly affect an ability of chewing a food. However, any device or method for measuring a masticatory ability due to a condition of arrangement and occlusion of teeth is not known.

Also, in artificial teeth, a maxillomandibular occlusal condition according to an arrangement condition of teeth, a grinding of the artificial teeth and a wear of teeth after use for a certain period affect an ability of chewing a food. However, any device or method for measuring a masticatory ability due to a condition of arrangement and occlusion of teeth is not known.

Specifically, a comparison between different dentures or between a denture before use and the same denture after use is not made, and therefore evaluation of a time for replacement of a denture or a masticatory ability of a denture can not be made. Also, a masticatory ability of a denture is influenced a great deal by an occlusal force, a chewing habit and a diet habit of a patient, and therefore appropriate dentures different according to patients. Consequently, it is desired a method for evaluating previously whether a masticatory ability of a denture for a certain patient is appropriate or not, at a fabrication of a denture.

If a masticatory ability of a denture can be recognized before the denture is put in a patient, it can be used as information for a treatment and a diagnosis of the patient and can also be put to use in next treatment.

Further, if the masticatory ability can be quantified, it can be determined whether the fabricated denture is appropriate or not by defining a threshold value, and it can be quantitatively evaluated how much masticatory ability the fabricated denture has.

SUMMERY OF THE INVENTION

The objects of the present invention is to provided an occlusion evaluation apparatus and an occlusion evaluation method that can evaluate a masticatory ability depending on an occlusal geometry of teeth without actually used by a human subject.

In order to achieve the above object, a first aspect of an occlusion evaluation apparatus according to the present invention comprises an input device, an arithmetic device and a display device, the input device being configured to input three dimensional data of geometries of maxillary molar teeth and mandibular molar teeth into the arithmetic device, the arithmetic device being configured to determine a geometry of a fluxion space which is defined between occlusal surfaces of the maxillary molar teeth and occlusal surfaces of the mandibular molar teeth when the maxillary molar teeth and the mandibular molar teeth are occluded, and to slidingly moves the maxillary molar teeth and the mandibular molar teeth with respect to each other to change an occlusal condition arbitrarily so that the geometry of the fluxion space is changed, and the display device being configured to display the geometry of the fluxion space in a visible manner, and to change the displayed geometry of the fluxion space in response to the change of the occlusal condition.

Further, a second aspect of an occlusion evaluation apparatus according to the present invention comprises an input device, an arithmetic device and a display device, the input device being configured to input three dimensional data of geometries of maxillary molar teeth and mandibular molar teeth into the arithmetic device, the arithmetic device being configured to determine a fluxion space which is defined between occlusal surfaces of the maxillary molar teeth and occlusal surfaces of the mandibular molar teeth when the maxillary molar teeth and the mandibular molar teeth are occluded, to slidingly moves the maxillary molar teeth and the mandibular molar teeth with respect to each other so as to change an occlusal condition arbitrarily, and to calculate a variation of a volume of the fluxion space with reference to an amount of a relative movement between the maxillary molar teeth and the mandibular molar teeth, and the display device being configured to display the variation of the volume of the fluxion space with reference to the amount of the relative movement.

According to these configurations, by checking a variation in size and shape of the fluxion space due to a masticatory movement, a magnitude of an effect to discharge a food ground by molar teeth from between teeth can be easily recognized, so that a masticatory ability of molar teeth can be evaluated independently of a muscle power and a chewing habit of a patient or an human subject.

Specifically, by displaying a cross-section, a position where the food is ground and position where the food escapes can be observed.

It is noted that the occlusion of a maxillary molar teeth and mandibular molar teeth in the occlusion evaluation apparatus according to the present invention may be performed so as to replicate an actual movement of a jaw of a patient measured by a jaw movement measuring device, alternatively so as to simulate an occlusal condition which is replicated in an articulator, for instance, an adjusting mechanism for an inclination of a sagittal condylar path, an angle of a balancing side lateral condylar path and an amount of an immediate side shift and an adjusting mechanism for an angle of a working side lateral condylar path, based on the data.

Further, the occlusion evaluation apparatus according to the second aspect of the present invention may read three dimensional data of geometries of plural sets of maxillary molar teeth and mandibular molar teeth so as to display volumes of the fluxion spaces in comparison to each other.

According to this construction, a deterioration of a masticatory ability of a denture due to wear and a variation in a masticatory ability of a denture due to grinding can be checked in a quantified manner. Also, a comparison of masticatory abilities between a current denture and a denture to be newly fabricated can be made. Specifically, if deteriorations of a masticatory ability of dentures due to wear is quantified and a graph for comparing the data of the respective dentures can be displayed, information of a certain patient are accumulated so as to facilitate fabricating of more appropriate denture for the patient.

In the occlusion evaluation apparatus according to the present invention, the fluxion space may be a space defined by a plane which includes two adjacent contact points between the maxillary molar teeth and mandibular molar teeth and which is perpendicular to the occlusal plane, the occlusal surfaces of the maxillary molar teeth, and the occlusal surfaces of the mandibular molar teeth, a space defined by a plane which includes two adjacent cusps of the maxillary molar teeth and which is perpendicular to the occlusal plane, a plane which includes two adjacent cusps of the mandibular molar teeth and which is perpendicular to the occlusal plane, the occlusal surfaces of the maxillary molar teeth, and the occlusal surfaces of the mandibular molar teeth, or a space defined by a plane which includes two adjacent widest contours of the maxillary molar teeth and which is perpendicular to the occlusal plane, a certain maxillary reference plane positioned above fossae of the maxillary molar teeth, a plane which includes two adjacent widest contours of the mandibular molar teeth and which is perpendicular to the occlusal plane, a certain mandibular reference plane positioned below fossae of the mandibular molar teeth, the occlusal surfaces of the maxillary molar teeth, and the occlusal surfaces of the mandibular molar teeth.

According to this construction, an extent to be compared can be easily determined.

The occlusion evaluation apparatus according to the present invention may display a volume of the fluxion space.

According to this construction, a masticatory ability can be recognized as a numerical figure.

The occlusion evaluation apparatus according to the present invention may determine a cross-section in which a cross-sectional area of the fluxion space gets smallest, so as to display the cross-section.

According to this construction, by the smallest cross-section, degrees of a wear and a grinding are best shown straight.

The occlusion evaluation apparatus according to the present invention, the three dimensional data of geometries of maxillary molar teeth and mandibular molar teeth may be modified.

According to this construction, a change of a masticatory ability of the denture due to grinding can be simulated, thereby the best grinding can be found.

The occlusion evaluation apparatus according to the present invention may calculate a variation of a cross-sectional area of the fluxion space in a cross-section perpendicular to the occlusal plane, with respect to a relative moving distance between the maxillary molar teeth and mandibular molar teeth and then to differentiate the calculated variation with respect to the relative moving distance, when changing the occlusal condition of the maxillary molar teeth and mandibular molar teeth, so as to display the differentiated variation.

According to this construction, a change of a masticatory ability in the course of a masticatory movement can be checked.

Further, an occlusion evaluation method according to the present invention includes reading three dimensional data of geometries of maxillary molar teeth and mandibular molar teeth into a computer, determining a fluxion space which is defined between occlusal surfaces of the maxillary molar teeth and occlusal surfaces of the mandibular molar teeth with occluding the maxillary molar teeth and the mandibular molar teeth by the computer, displaying a geometry of the fluxion space in a visible manner on a display device of the computer, and slidingly moving the maxillary molar teeth and the mandibular molar teeth with respect to each other on the computer to change an occlusal condition arbitrarily so that the geometry of the displayed fluxion space is changed according to the occlusal condition.

According to the present invention, by figuring out a dimension and a geometry of the fluxion space, a masticatory ability of the molar teeth can be evaluated independently of a muscular power and a chewing habit of a patient or a human subject.

Further, according to the present invention, by accumulating data of a plurality of dentures, a masticatory ability involving the chewing habit of a patient can be visualized and quantified, so that an accurate diagnosis and fabrication of better denture can be made.

DETAILED DESCRIPTION OF THE PREFERRED EMBODIMENT

Figure 1:
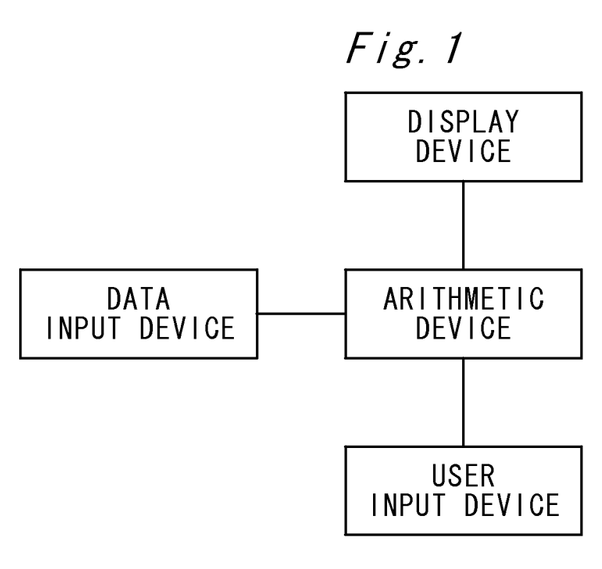
FIG. 1 is a block diagram showing a configuration of a occlusion evaluation apparatus as first embodiment of the present invention.

Hereinafter, an embodiment of the present invention is described with referring drawings. An occlusion evaluation apparatus according to the present invention can be realized using a computer and the like that comprises an arithmetic device, a data input device, a display device and a user input device as shown in FIG. 1.

The arithmetic device can be substantialized using a personal computer and a software program, while the arithmetic device may be exclusively designed. The data input device can be not only a device such as three dimensional scanner reading directory three dimensional shape, but also a device for inputting three dimensional data which is read by an external three dimensional scanner and the like into the arithmetic device, such as a media reading device, for instance a memory device or a disc drive, or a data communication device. The display device may be a common display. As the user input device, a generalized input device such as a keyboard and a mouse can be used.

The occlusion evaluation apparatus according to the present invention reads three dimensional geometric data of maxillary molar teeth and mandibular molar teeth through the data input device into the arithmetic device, occludes the maxillary molar teeth and the mandibular molar teeth on the arithmetic device, calculates a three dimensional geometry of a fluxion space which is defined between occlusal surfaces of the maxillary molar teeth and occlusal surfaces of the mandibular molar teeth, and displays the three dimensional geometry of the fluxion space on the display device. To display the fluxion space, a method used for computer graphics, such as wire frame and ray tracing can be applied.

Figure 2:
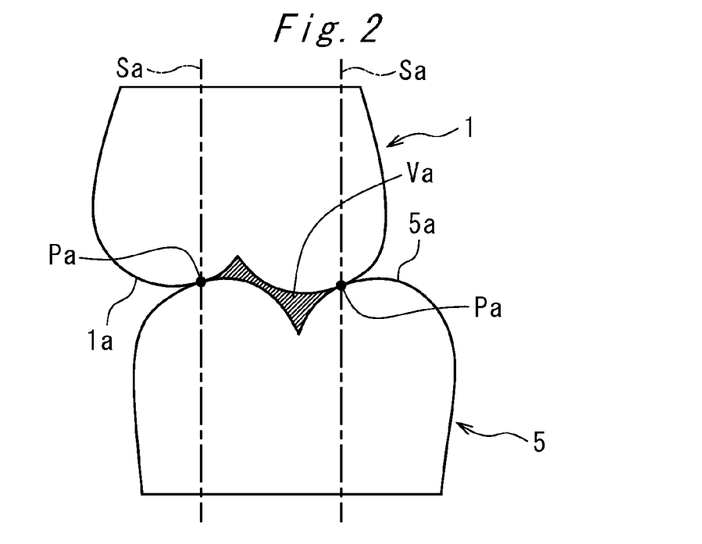
FIG. 2 is a cross-sectional view of a fluxion space according to a first aspect of the preset invention.
Figure 3:
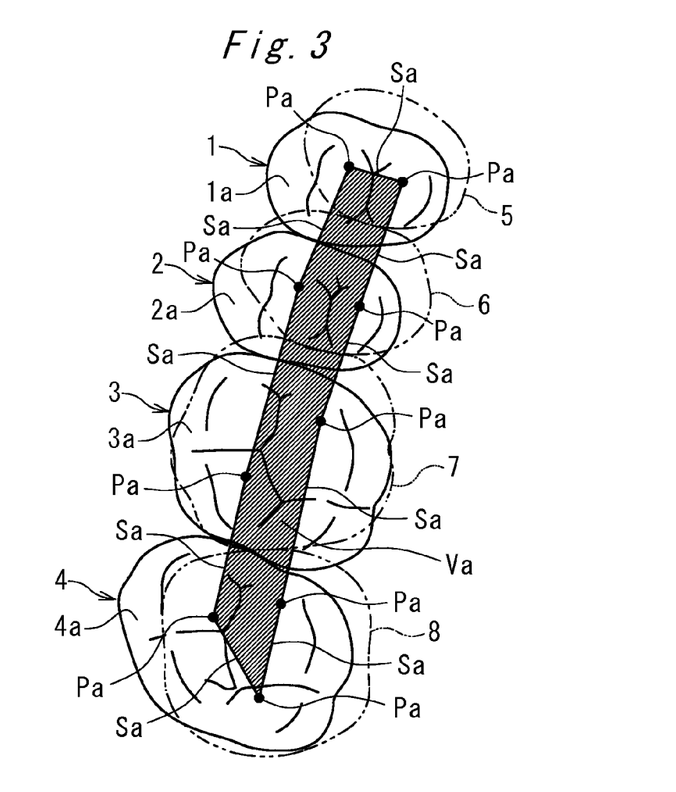
FIG. 3 is a plane view of the fluxion space in FIG. 2.
Figure 4:
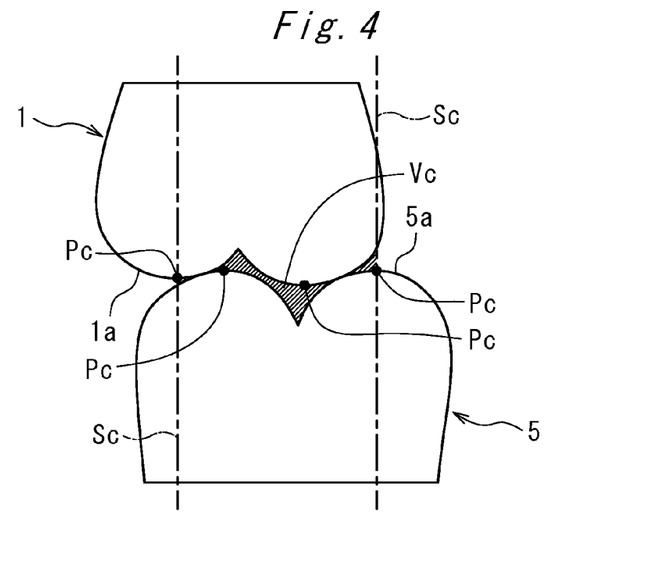
FIG. 4 is a cross-sectional view of a fluxion space according to a second aspect of the preset invention.
Figure 5:
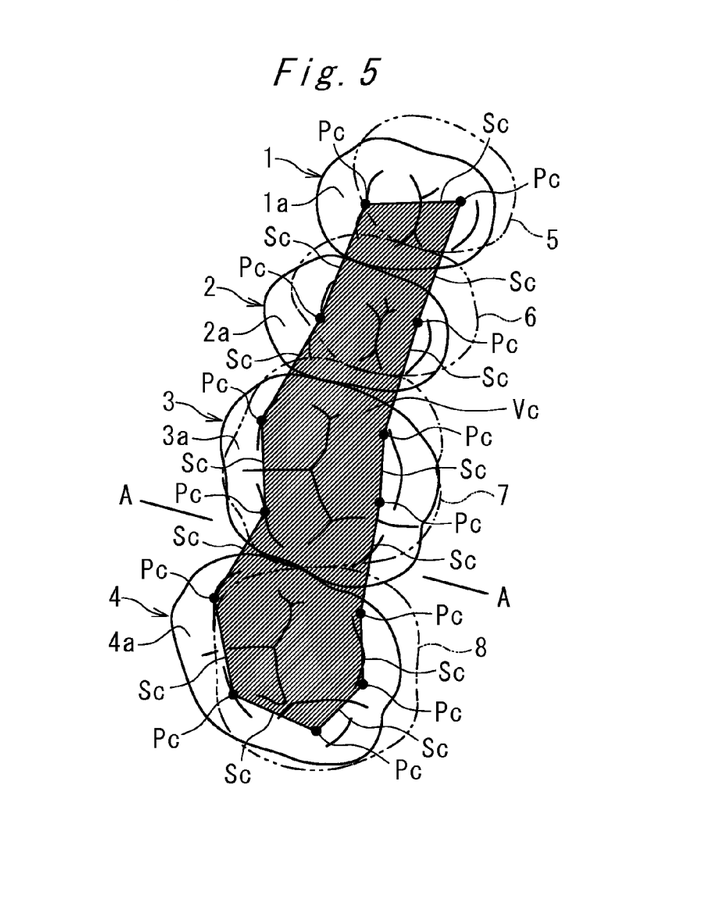
FIG. 5 is a plane view of the fluxion space in FIG. 4.
Figure 6:
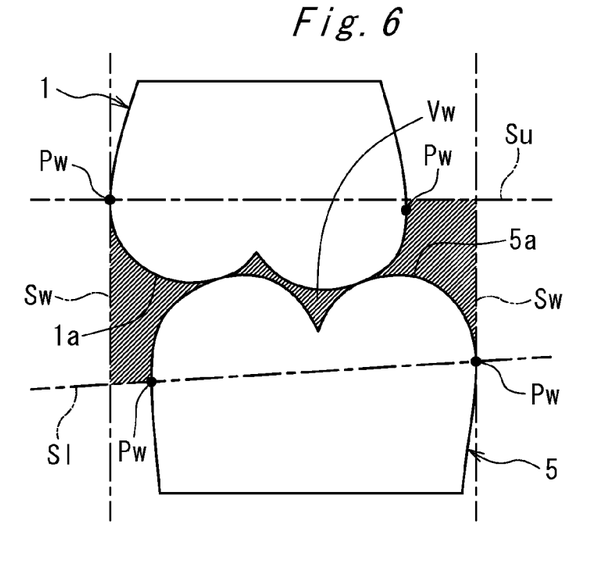
FIG. 6 is a cross-sectional view of a fluxion space according to a third aspect of the preset invention.
Figure 7:
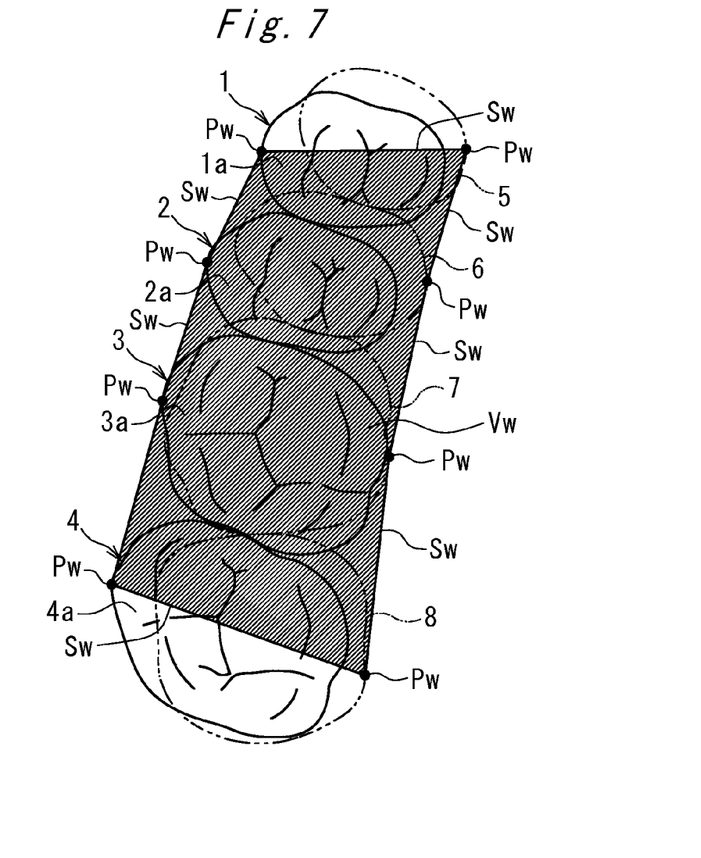
FIG. 7 is a plane view of the fluxion space in FIG. 6.
Figure 8:
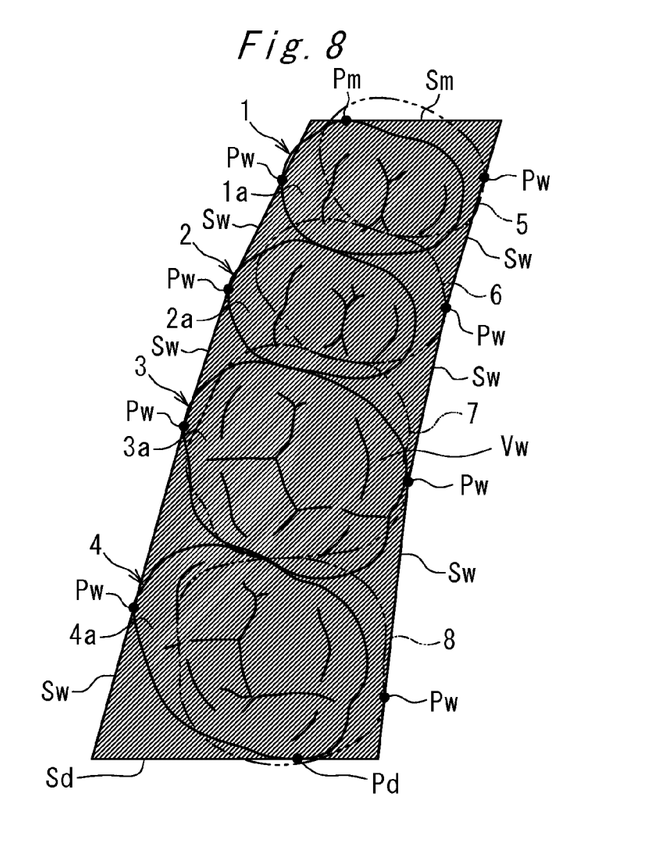
FIG. 8 is a plane view of a fluxion space alternative to that in FIG. 7.

FIGS. 2 and 3 show a fluxion space Va that is a first aspect related to the embodiment of the present invention, FIGS. 4 and 5 show a fluxion space Vc that is a second aspect related to the embodiment of the present invention, and FIGS. 6 and 7 show a fluxion space Vw that is a third aspect related to the embodiment of the present invention.

The fluxion space Va of the first aspect is a space defined by planes Sa which include two adjacent contact points Pa between the maxillary molar teeth (first premolar tooth 1, second premolar tooth 2, first molar tooth 3, second molar tooth 4) and mandibular molar teeth (first premolar tooth 5, second premolar tooth 6, first molar tooth 7, second molar tooth 8) and which are perpendicular to the occlusal plane, the occlusal surfaces 1a, 2a, 3a, 4a of the maxillary molar teeth 1, 2, 3, 4, and the occlusal surfaces 5a, 6a, 7a, 8a of the mandibular molar teeth 5, 6, 7, 8.

The fluxion space Vc of the second aspect is a space defined by planes Sc which include two adjacent cusps Pc of the maxillary molar teeth 1, 2, 3, 4 and which is perpendicular to the occlusal plane, a plane which include two adjacent cusps Pc of the mandibular molar teeth 5, 6, 7, 8 and which are perpendicular to the occlusal plane, the occlusal surfaces 1a, 2a, 3a, 4a of the maxillary molar teeth 1, 2, 3, 4, and the occlusal surfaces 5a, 6a, 7a, 8a of the mandibular molar teeth 5, 6, 7, 8.

The fluxion space Vw of the third aspect is a space defined by planes Sw which include two adjacent widest contours Pw of the maxillary molar teeth 1, 2, 3, 4 and which are perpendicular to the occlusal plane, planes Sw which include two adjacent widest contours Pw of the mandibular molar teeth 5, 6, 7, 8 and which are perpendicular to the occlusal plane, a certain maxillary reference plane Su positioned above the occlusal plane 1a, 2a, 3a, 4a of the maxillary molar teeth 1, 2, 3, 4, a certain mandibular reference plane Sl positioned below the occlusal surfaces 5a, 6a, 7a, 8a of the mandibular molar teeth 5, 6, 7, 8, the occlusal surfaces 1a, 2a, 3a, 4a of the maxillary molar teeth 1, 2, 3, 4, and the occlusal surfaces 5a, 6a, 7a, 8a of the mandibular molar teeth 5, 6, 7, 8.

The occlusal plane technically means a plane defined by three points which are a contact point on a cutting edge of a mandibular central incisor and both distal buccal cusps of the left and right mandibular second molar teeth. However, in the present invention the occlusal plane may be any plane equivalent to the above plane. For instance, in a case where data of anterior teeth are missing, a plane defined by three points which are a mesial buccal cusp of the left or right mandibular first premolar tooth and both distal buccal cusps of the left and right mandibular second molar teeth may be assumed as the occlusal plane, and in a case where data of only left or right side molar teeth are existing, a plane defined by three points which are a mesial buccal cusp of the mandibular first premolar tooth, a cusp of the mandibular second molar teeth and a mesial lingual cusp of the mandibular first molar tooth may be assumed as the occlusal plane. As a further alternative, a reference plane for reading the geometry of the mandibular molar tooth (a plane being constant in a vertical axial position in Cartesian system), that is a basic plane of the mandibular molar teeth or gum of the mandibular molar teeth in the data may be assumed as the occlusal plane. It is noted that the occlusal surface is a term referring to a concavo-convex surface on the top of the molar teeth, and therefore is clearly distinguished from the occlusal plane.

In the present invention, the fluxion spaces Va, Vc, Vw are normally calculated one for each of left and right sides. However, in a case where a molar tooth is missing, the fluxion spaces may be calculated in a manner divided into mesial side and distal side, or for every pair of opposing teeth. Further, in a case having a third molar tooth, the fluxion spaces Va, Vc, Vw may be calculated extendedly to the third molar tooth.

In the calculation of the fluxion space Vw of the third aspect, in a case where dental arches can be determined, the widest contours Pw may be lingual side widest contours and buccal side widest contours. However, as shown in FIG. 7, the widest contours Pw may be points where the three dimensional data in Cartesian system gets the maximum or the minimum in the lateral axial direction.

Further, the fluxion spaces Va, Vc, Vw shown in FIGS. 3, 5, 7 are defined as spaces closed in the mesiodistal direction respectively by a plane Sa including two adjacent contact points Pa on the first premolar tooth and another plane Sa including two adjacent contact points Pa on the second molar tooth, by a plane including two adjacent cusps Pc of the first premolar tooth and another plane including two adjacent cusps Pc of the second molar tooth and by a plane Sc including two widest contours Pw in the lateral direction (the buccolingual direction) of the first premolar tooth and another plane Sc including two widest contours Pw in the buccolingual direction of the second molar tooth. However, in an alternative to the fluxion space Vw of the third aspect, a tangential plane Sm at a widest contour Pm of the first premolar tooth in the mesial direction or an axial direction of the Cartesian system, and a tangential plane Sd at a widest contour Pd of the second molar tooth in the distal direction or an axial direction of the Cartesian system determine end faces in mesiodistal direction of the fluxion space Vw. Similarly, end faces in mesiodistal direction of the fluxion space Va of the first aspect and end faces in mesiodistal direction of the fluxion space Vc of the second aspect may be defined by a plane determined by a different rule.

Furthermore, in the calculation of the fluxion space Vw shown in FIG. 6, the maxillary reference plane Su and mandibular reference plane Sl are planes which include respectively three points of predetermined widest contours Pw (for instance, a buccal widest contour of the first premolar teeth 1, 5 and a buccal widest contour and a lingual widest contour of the second molar teeth 4, 8). However, the maxillary reference plane Su may be any plane positioned above all of fossae of the maxillary molar teeth 1, 2, 3, 4, and the mandibular reference plane Sl may be any plane positioned below all of fossae of the mandibular molar teeth 5, 6, 7, 8. For instance, the maxillary reference plane Su and the mandibular reference plane Sl may be planes respectively include a specific widest contour of a predetermined molar tooth and parallel to the occlusal plane.

Further, when calculating the fluxion space Va of the first aspect and the fluxion space Vc of the second aspect, there is a case where a limit in a direction perpendicular to the occlusal plane can not defined by the occlusal surfaces, for instance at interdentium. Therefore, for the calculation of the fluxion space Va of the first aspect and the fluxion space Vc of the second aspect, a maxillary reference plane Su and a mandibular reference plane Sl may be determined, similar to defining the fluxion space Vw of the third aspect.

The occlusion evaluation apparatus according to the present invention preferably configured to display a shape of the fluxion space which is chosen among the fluxion space Va, the fluxion space Vc and the fluxion space Vw by a user (a doctor or a dental technician) via the user input device.

Further, the occlusion evaluation apparatus according to the present invention, together with the display of the fluxion space Va, Vc, Vw, indicates a volume of the fluxion space so that a masticatory ability can be quantitively recognized.

Further, the occlusion evaluation apparatus according to the present invention preferably calculates automatically an intercuspal occlusal position, an occlusal position, a centric occlusion and an initial occlusal contact position where the fluxion space Va, Vc or Vw is maximized, and allow a user to chose an occlusal position among the calculated occlusal positions so as to display the chosen occlusal position.

Furthermore, the occlusion evaluation apparatus according to the present invention preferably configured to change the occlusal condition of the maxillary molar teeth 1, 2, 3, 4 and the mandibular molar teeth 5, 6, 7, 8. If the computer calculates sliding movement between the maxillary molar teeth 1, 2, 3, 4 and the mandibular molar teeth 5, 6, 7, 8, for instance, in response to that the user inputs any desired direction to move the maxillary molar teeth 1, 2, 3, 4 with respect to the mandibular molar teeth 5, 6, 7, 8, so as to display the change in the geometry of the fluxion space Va, Vc, Vw in real time, the change of the fluxion space Va, Vc, Vw due to a masticatory movement can be visually recognized.

Figure 9:
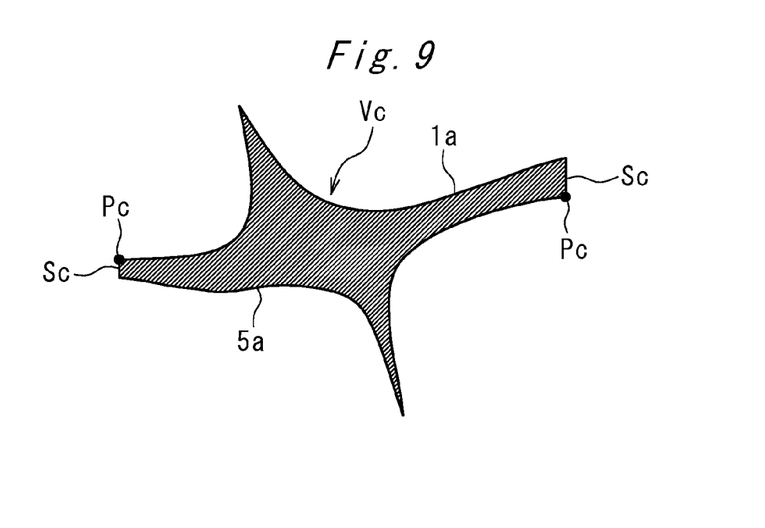
FIG. 9 is a cross-sectional view along A-A line in FIG. 5.

Further, the occlusion evaluation apparatus according to the present invention preferably displays a geometry and a cross-sectional area of any desired cross-section of the fluxion space Va, Vc, Vw. For example, FIG. 9 shows a cross-sectional view of the fluxion space Vc in FIG. 5 along A-A line. Further more, if the occlusion evaluation apparatus calculates a position of a cross-section which has minimum cross-sectional area to display the position on the screen, the most significant cross-section in the fluxion space Va, Vc, Vw for a mastication can be notified to the user.

In addition, the occlusion evaluation apparatus according to the present invention preferably can display variations in the volume of the fluxion space Va, Vc, Vw and in the cross-sectional area of the fluxion space Va, Vc, Vw at a specific position while any desired sliding movement between the maxillary molar teeth 1, 2, 3, 4 and the mandibular molar teeth 5, 6, 7, 8, with reference to the relative displacement between the maxillary molar teeth 1, 2, 3, 4 and the mandibular molar teeth 5, 6, 7, 8, in a chart. More preferably, the variations are differentiated and double differentiated with respect to the relative displacement of the movement to determine a rate of change of the fluxion space Va, Vc, Vw, and then display the rate of change in a chart so that the smoothness of the masticatory movement can be checked.

Also, the occlusion evaluation apparatus according to the present invention preferably is capable of modifying the three dimensional data of the maxillary molar teeth 1, 2, 3, 4 and the mandibular molar teeth 5, 6, 7, 8. Thereby, an optimum design of a denture or a simulation of grinding of the teeth can be made.

The occlusion evaluation apparatus according to the present invention not only determines an optimum geometry of denture by means of the fluxion space Va, Vc, Vw, but also can evaluate a masticatory ability of denture including a chewing habit and the like of a patient, by evaluating a difference in masticatory ability between a new denture and a worn denture after use.

REFERENCE SIGN LIST

1 . . . first maxillary premolar tooth
2 . . . second maxillary premolar tooth
3 . . . first maxillary molar tooth
4 . . . second maxillary molar tooth
5 . . . first mandibular premolar tooth
6 . . . second mandibular premolar tooth
7 . . . first mandibular molar tooth
8 . . . second mandibular molar tooth
Pa . . . contact point
Pc . . . cusp
Pw . . . widest contour
Sa . . . plane includes contact points
Sc . . . plane includes cusps
Sw . . . plane includes widest contours
Su . . . maxillary reference plane
Sl . . . mandibular reference plane

What is claimed is:

1. An occlusion evaluation apparatus comprising an input device, an arithmetic device and a display device, wherein
the input device is configured to input three dimensional data of geometries of maxillary molar teeth and mandibular molar teeth into the arithmetic device,
the arithmetic device is configured to determine a geometry of a fluxion space which is defined between occlusal surfaces of the maxillary molar teeth and occlusal surfaces of the mandibular molar teeth when the maxillary molar teeth and the mandibular molar teeth are occluded, and to slidingly moves the maxillary molar teeth and the mandibular molar teeth with respect to each other to change an occlusal condition arbitrarily so that the geometry of the fluxion space is changed, and
the display device is configured to display the geometry of the fluxion space in a visible manner, and to change the displayed geometry of the fluxion space in response to the change of the occlusal condition.

2. The occlusion evaluation apparatus according to claim 1, wherein
the fluxion space is:
a space defined by a plane which includes two adjacent contact points between the maxillary molar teeth and mandibular molar teeth and which is perpendicular to the occlusal plane, the occlusal surfaces of the maxillary molar teeth, and the occlusal surfaces of the mandibular molar teeth;
a space defined by a plane which includes two adjacent cusps of the maxillary molar teeth and which is perpendicular to the occlusal plane, a plane which includes two adjacent cusps of the mandibular molar teeth and which is perpendicular to the occlusal plane, the occlusal surfaces of the maxillary molar teeth, and the occlusal surfaces of the mandibular molar teeth; or
a space defined by a plane which includes two adjacent widest contours of the maxillary molar teeth and which is perpendicular to the occlusal plane, a certain maxillary reference plane positioned above fossae of the maxillary molar teeth, a plane which includes two adjacent widest contours of the mandibular molar teeth and which is perpendicular to the occlusal plane, a certain mandibular reference plane positioned below fossae of the mandibular molar teeth, the occlusal surfaces of the maxillary molar teeth, and the occlusal surfaces of the mandibular molar teeth.

3. The occlusion evaluation apparatus according to claim 1, wherein the arithmetic device is configured to determine a cross-section in which a cross-sectional area of the fluxion space gets smallest, and the display device is configured to display the cross-section determined by the arithmetic device.

4. The occlusion evaluation apparatus according to claim 1, wherein the arithmetic device is capable of modifying the three dimensional data of geometries of maxillary molar teeth and mandibular molar teeth.

5. The occlusion evaluation apparatus according to claim 1, wherein the arithmetic device is configured to calculate a variation of a cross-sectional area of the fluxion space in a cross-section perpendicular to the occlusal plane, with reference to a relative moving distance between the maxillary molar teeth and mandibular molar teeth, when changing the occlusal condition of the maxillary molar teeth and mandibular molar teeth, and to differentiate the variation calculated with respect to the relative moving distance, and the display device is configured to display the differentiated variation of the cross-sectional area.

6. An occlusion evaluation apparatus comprising an input device, an arithmetic device and a display device, wherein
the input device is configured to input three dimensional data of geometries of maxillary molar teeth and mandibular molar teeth into the arithmetic device,
the arithmetic device is configured to determine a fluxion space which is defined between occlusal surfaces of the maxillary molar teeth and occlusal surfaces of the mandibular molar teeth when the maxillary molar teeth and the mandibular molar teeth are occluded, to slidingly moves the maxillary molar teeth and the mandibular molar teeth with respect to each other so as to change an occlusal condition arbitrarily, and to calculate a variation of a volume of the fluxion space with reference to an amount of a relative movement between the maxillary molar teeth and the mandibular molar teeth, and
the display device is configured to display the variation of the volume of the fluxion space with reference to the amount of the relative movement.

7. The occlusion evaluation apparatus according to claim 6, wherein the arithmetic device is configured to calculate volumes of the respective fluxion spaces with three dimensional data of geometries of plural sets of maxillary molar teeth and mandibular molar teeth, and the display device is configured to display the volumes of the fluxion spaces in comparison.

8. The occlusion evaluation apparatus according to claim 6, wherein
the fluxion space is:
a space defined by a plane which includes two adjacent contact points between the maxillary molar teeth and mandibular molar teeth and which is perpendicular to the occlusal plane, the occlusal surfaces of the maxillary molar teeth, and the occlusal surfaces of the mandibular molar teeth;
a space defined by a plane which includes two adjacent cusps of the maxillary molar teeth and which is perpendicular to the occlusal plane, a plane which includes two adjacent cusps of the mandibular molar teeth and which is perpendicular to the occlusal plane, the occlusal surfaces of the maxillary molar teeth, and the occlusal surfaces of the mandibular molar teeth; or
a space defined by a plane which includes two adjacent widest contours of the maxillary molar teeth and which is perpendicular to the occlusal plane, a certain maxillary reference plane positioned above fossae of the maxillary molar teeth, a plane which includes two adjacent widest contours of the mandibular molar teeth and which is perpendicular to the occlusal plane, a certain mandibular reference plane positioned below fossae of the mandibular molar teeth, the occlusal surfaces of the maxillary molar teeth, and the occlusal surfaces of the mandibular molar teeth.

9. The occlusion evaluation apparatus according to claim 6, wherein the arithmetic device is configured to determine a cross-section in which a cross-sectional area of the fluxion space gets smallest, and the display device is configured to display the cross-section determined by the arithmetic device.

10. The occlusion evaluation apparatus according to claim 6, wherein the arithmetic device is capable of modifying the three dimensional data of geometries of maxillary molar teeth and mandibular molar teeth.

11. The occlusion evaluation apparatus according to claim 6, wherein the arithmetic device is configured to calculate a variation of a cross-sectional area of the fluxion space in a cross-section perpendicular to the occlusal plane, with reference to a relative moving distance between the maxillary molar teeth and mandibular molar teeth, when changing the occlusal condition of the maxillary molar teeth and mandibular molar teeth, and to differentiate the variation calculated with respect to the relative moving distance, and the display device is configured to display the differentiated variation of the cross-sectional area.

12. An occlusion evaluation method comprising
reading three dimensional data of geometries of maxillary molar teeth and mandibular molar teeth into a computer,
determining a fluxion space which is defined between occlusal surfaces of the maxillary molar teeth and occlusal surfaces of the mandibular molar teeth with occluding the maxillary molar teeth and the mandibular molar teeth by the computer,
displaying a geometry of the fluxion space in a visible manner on a display device of the computer, and
slidingly moving the maxillary molar teeth and the mandibular molar teeth with respect to each other on the computer to change an occlusal condition arbitrarily so that the geometry of the displayed fluxion space is changed according to the occlusal condition.

13. An occlusion evaluation method comprising
reading three dimensional data of geometries of maxillary molar teeth and mandibular molar teeth in to a computer,
determining a fluxion space which is defined between occlusal surfaces of the maxillary molar teeth and occlusal surfaces of the mandibular molar teeth with occluding the maxillary molar teeth and the mandibular molar teeth to calculate a volume of the fluxion space by the computer,
displaying the volume of the fluxion space on a display device of the computer,
slidingly moving the maxillary molar teeth and the mandibular molar teeth with respect to each other on the computer to change an occlusal condition arbitrarily so that the volume of the fluxion space displayed on the display device is changed, and
calculating a variation of the volume of the fluxion space with respect to the relative moving distance between the maxillary molar teeth and the mandibular molar teeth so as to display on the display device.

* * * * *